(12) United States Patent
Gagnon

(10) Patent No.: US 9,927,427 B2
(45) Date of Patent: Mar. 27, 2018

(54) EXOSOME RECOVERY METHODS WITH LOW MOLECULAR WEIGHT ORGANIC ZWITTERIONS

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/031,660

(22) PCT Filed: Oct. 15, 2014

(86) PCT No.: PCT/SG2014/000485
§ 371 (c)(1),
(2) Date: Apr. 22, 2016

(87) PCT Pub. No.: WO2015/060784
PCT Pub. Date: Apr. 30, 2015

(65) Prior Publication Data
US 2016/0266097 A1 Sep. 15, 2016

Related U.S. Application Data

(60) Provisional application No. 61/895,338, filed on Oct. 24, 2013.

(51) Int. Cl.
*G01N 33/50* (2006.01)
*A61K 35/12* (2015.01)
*B01D 15/36* (2006.01)

(52) U.S. Cl.
CPC ......... *G01N 33/5076* (2013.01); *A61K 35/12* (2013.01); *B01D 15/364* (2013.01); *G01N 33/5005* (2013.01)

(58) Field of Classification Search
CPC .. A61K 35/12; B01D 15/364; G01N 33/5005; G01N 33/5076
See application file for complete search history.

(56) References Cited

U.S. PATENT DOCUMENTS

| | | | |
|---|---|---|---|
| 6,812,023 B1 | 11/2004 | Lamparski et al. | |
| 2012/0208175 A1 | 8/2012 | Newman et al. | |
| 2012/0244212 A1* | 9/2012 | Guilford | A61K 45/06 424/450 |
| 2012/0316220 A1* | 12/2012 | Ward | A01K 67/0333 514/44 A |

FOREIGN PATENT DOCUMENTS

| EP | 2 713 163 | 4/2014 |
|---|---|---|
| WO | WO 2012/169970 | 12/2012 |

OTHER PUBLICATIONS

Kim et al. Noble Polymeric Surface Conjugated with Zwitterionic Moieties . . . Bioconjugate Chemistry. Oct. 1, 2012. vol. 23, pp. 2114-2120.*
Solcyc Webpage. MetaCyc Compound: homotaurine. http://solcyc.solgenomics.net/META/NEW-IMAGE?type=COMPOUND&object= CPD-11725. Created Aug. 24, 2009, downoladed Mar 11, 2017.*
Tauro et al. Two Distinct Populations of Exosomes Are Released . . . Molecular & Cellular Proteomics 12.3. pp. 587-598. Dec. 10, 2012.*
Zumaquero et al. Exosomes from human lymphobastoid B cells express enzymatically active CD38 . . . Experimental Cell Research. Jun. 4, 2010, vol. 316, pp. 2692-2706.*
Gagon, "Technology trends in antibody purification" Journal of Chromatography I, 1221, (2012), pp. 57-70.
Kang et al., "Proteomic analysis of exosomes from human neural stem cells by flow field-flow fractionation and nonoflow liquid chromatography-Tandem mass spectrometry", Journal of proteome research, 2008, 7, pp. 3475-3480.
Lasser et al., "Isolation and characterization of RNA-containing exosomes", Jove Journal of Visualized Experiments, 2012, 59, e3037, pp. 1-6, URL: http://www.jove.com/video/3037.
Muller et al., "Mixed electrolytes in hydrophobic interaction chromatography", J. Sep. Sci. 2013, 36, pp. 1327-1334.
Sokolova et al., "Characterisation of exosomes derived from human cells by nanoparticle tracking analysis and scanning electron microscopy", Colloids and Surfaces B, Biointerfaces 87, (2011), pp. 146-150.
Vincent-Schneider et al., "Exosomes bearing HLA-DR1 molecules need dendritic cells to efficiently stimulate specific T cells", International Immunology, 2002, vol. 14, No. 7, pp. 713-722.
Vlassov et al., "Exosomes: Current knowledge of their composition, biological functions, and diagnostic and therapeutic potentials", Biochimica et Biophysica Acta 1820, (2012), pp. 940-948.
Conde-Vancells Javier et al, "Isolation of Urinary Exosomes from Animal Models to Unravel Noninvasive Disease Biomarkers", Methods in Molecular Biology, Aug. 2012, Chapter 21, vol. 909, pp. 321-340.
Yang, Xi et al, "Circulating extracellular vesicles as a potential source of new biomarkers of drug-induced liver injury", Toxicology Letters, Jan. 2014, vol. 225, pp. 401-406.
International Search Report dated Nov. 24, 2014 in International Patent Application No. PCT/SG2014/000485 (4 Pages).
Extended European Search Report dated May 23, 2017 for EP14855837.2.
Jorgensen et al., "Extracellular Vesicle (EV) Array: microarray capturing of exosomes and other extracellular vesicles for multiplexed phenotyping," Journal of Extracellular Vesicles, vol. 2, No. 1, Jun. 18, 2013, p. 20920.

(Continued)

*Primary Examiner* — Jeffrey E Russel
(74) *Attorney, Agent, or Firm* — Pillsbury Winthrop Shaw Pittman LLP

(57) ABSTRACT

A method of isolating exosomes includes conducting at least one purification step in the presence of an organic zwitterion having a molecular weight of less than about 350 Daltons, a buffering pK of a negatively charged portion of the organic zwitterion is at least one full pH unit below an operating pH at which the at least one purification step is conducted, and a buffering pK of the positively charged portion of the organic zwitterion is at least one full pH unit above the operating pH.

21 Claims, No Drawings

(56) References Cited

OTHER PUBLICATIONS

Anonymous (Author Unknown), "Exosome Immunoprecipitation (Protein A) / Exosome Immunoprecipitation (Protein G)," Jun. 1, 2012, Invitrogen, Retrieved from the Internet: URL: https://tools. thermofisher.com/content/sfs/manuals/exosome_immunoprecipitation_A_G_man.pdf [retrieved on May 4, 2017].

Omwandho et al., "Ovine placental eluate immunoglobulins recognize isologous and third party acid-treated trophoblast microvesicle antigens in vitro," Journal of the South African Veterinary Association, vol. 77, No. 1, Jun. 6, 2006, pp. 24-27.

* cited by examiner

EXOSOME RECOVERY METHODS WITH LOW MOLECULAR WEIGHT ORGANIC ZWITTERIONS

This patent application is a national stage filing of International Patent Application Number PCT/SG2014/000485 filed on Oct. 15, 2014 entitled EXOSOME RECOVERY METHODS WITH LOW MOLECULAR WEIGHT ORGANIC ZWITTERIONS, which claims the benefit of U.S. Provisional Patent Application No. 61/895,338 filed on Oct. 24, 2013.

FIELD

Embodiments disclosed herein relate to the methods of purifying exosomes, and more particularly to the use of low molecular weight organic zwitterions in purifying exosomes.

BACKGROUND

Exosomes are cell-derived vesicles of about 30 to 120 nm associated with a wide range of biological fluids. Although their biological functions are not yet fully characterized, their potential utility in various diagnostic and therapeutic applications has been considered. They are commonly purified by techniques that discriminate on the basis of size, such as ultracentrifugation, flow cytometry, filtration, size exclusion chromatography, and field flow fractionation (Kang, D., et al J. Proteome Res., 7 (2008) 3475-3480; Lasser, C., et al, J. Vis. Exp. 59 (2012) e3037; Sokolova, V., et al, Colloids Surf. B: Biointerfaces, 87 (2011) 146-150).

The composition of exosomes is discussed by A. Vlassov et al (Biochim. Biophys. Acta 1820 (2012) 940-948). They contain a nucleotide and protein cargo, consisting of an estimated less than 10,000 nucleotide units and less than 300 proteins. These are enclosed within a lipid-bilayer membrane that is variously enriched, depending on the source of the exosomes, with cholesterol, ceramides, sphingolipids, and phosphoglycerides with long saturated fatty acyl chains. The outer surface also bears saccharide groups including mannose, polylactosamine, alpha-2,6-sialic acid, and complex N-linked glycans.

Glycine is a naturally occurring amino acid that exists in zwitterionic form at physiological pH. It is used frequently in the field of exosome research at a concentration of 100 mM to quench unreacted amino-reactive aldehydes on solid particles following covalent linkage of exosomes to such particles (Vincent-Schneider, H., et al, Intl. Immunol., 14 (2002) 713-722). It has also been described as bulking agent in formulations of purified exosomes (H. Lamparski et al, U.S. Pat. No. 6,812,023 B1, 2004). Glycine is known to promote non-specific interactions between proteins and hydrophobic surfaces (Gagnon, P., J. Chromatog. A. 1221 (2012) 57-70; Muller, E., et al, J. Sep. Sci., 36 (2013) 1327-1334). The high lipid content of cell membranes is understood to mediate elevated surface hydrophobicity.

SUMMARY

In some aspects, embodiments disclosed herein relate to methods of isolating exosomes comprising conducting at least one purification step in the presence of an organic zwitterion having a molecular weight of less than about 350 Daltons, wherein a buffering pK of a negatively charged portion of the organic zwitterion is at least one full pH unit below an operating pH at which the at least one purification step is conducted, and a buffering pK of the positively charged portion of the organic zwitterion is at least one full pH unit above the operating pH.

DETAILED DESCRIPTION

It has been discovered that the combination of exosomes with small organic zwitterions can enhance exosome recovery during purification. Without being bound by theory, enhanced recovery appears to be mediated by a decrease in non-specific interactions between exosomes and surfaces with which they come into contact. This is seemingly counterintuitive because glycine, an example of one appropriate species of zwitterion, is known to promote non-specific interactions between proteins and hydrophobic surfaces, and the lipid component of the outer exosome membrane is understood to be strongly hydrophobic. The apparent ability of qualified zwitterions to reduce non-specific interactions may reflect an increase in exosome solubility mediated by the ability of zwitterions to elevate the polarity of aqueous solutions. Surfaces with which exosomes may interact non-specifically during purification may include filtration media and chromatography media. Whether decreasing non-specific interactions and increasing solubility are distinct phenomena or different aspects of the same phenomenon remains to be elucidated, but in either case combining exosomes with zwitterions, in accordance with embodiments disclosed herein, may lead to improved exosome recovery during purification.

Small organic zwitterions suitable for practicing the methods disclosed herein particularly include the amino acid glycine, with a molecular weight of about 75 Daltons (Da), or alanine, with a molecular weight of about 89 Da. Glycine consists of a central carbon linked to a primary amino group, a carboxyl group, and two hydrogen atoms, where the charges reside on opposite sides of the molecule. Due to the placement and distance between the amino and carboxyl groups, the zwitterionic form has an elevated dipole moment, which has the effect of increasing the bulk dielectric constant of aqueous solutions in which it resides. Glycine analogues such as betaine, taurine, and taurobetaine have essentially similar effects for the same reasons, except that in betaine the amino group is chemically modified (tri-methylated) to maintain its positive charge at pH values greater than 9; and in taurine the carboxyl group is substituted with a sulfo group to maintain its negative charge at pH less than 2; and in taurinobetaine, both the amino and carboxyl groups are modified so that the molecule is zwitterionic over the entire range from pH of about 3 to about 12. Similar or related structures, such as diamino acids, triamino acids, and larger multiples may be more effective at lower concentration because of their larger dipole moment, created by the larger distance between the positive and negative charges. Examples of such compounds include, but are not limited to, glycylglycine, and glycylglycylglycine, among many others up to penta-amino acids of homogeneous or heterogeneous composition. As in these examples, which bear the respective charged groups at opposite termini of the molecule, and where side groups on the intermediate carbons are substantially uncharged, so qualified are other zwitterions that bear opposite charges at opposite termini of a molecule with at least one intermediate carbon, and where the side groups on the intermediate carbons are substantially uncharged.

In some embodiments, glycine or alanine may be particularly useful because they are FDA approved USP-listed inactive ingredients known to be safe for human injection.

Glycine and alanine may be further useful because they are also widely available from multiple suppliers at low cost.

As used herein, glycine is provided as a non-exclusive example for the purpose of describing embodiments of the invention and should not be construed as limiting the invention. In accordance with some embodiments, glycine may be present at a concentration of 5 mM, 10 mM, 20 mM, 50 mM, 100 mM or higher, including up to 1 M, 2 M, or saturated (about 3 M). It may be beneficial in some such embodiments to employ a concentration of 100 mM or less to keep the osmolarity reasonably close to normal physiological values. Experimental data indicate that when exosomes are combined with 100 mM glycine in aqueous solution the beneficial effects to purification are at least as good as obtained at 1 M glycine. In some embodiments, the concentration of glycine may exceed 1 M, 2 M, 3 M, or may be saturated.

Glycine or other zwitterionic agents disclosed herein may be combined with one or more so-called zwitterionic buffers, such as Hepes (hydroxyethylpiperazine ethanesulfonic acid). Hepes has a pK of about 7 and is commonly used as an exosome buffering agent at concentrations of about 10 to about 20 mM. Such agents are not counted among the zwitterions creating the disclosed effect when they are used for buffering, within 1 pH unit of their pK, because in these cases the amino group is partially ionized, leaving the species with a non-neutral charge, which is believed to diminish its dipole moment and ability to elevate the dielectric constant of the solvent.

In some embodiments, glycine or other zwitterionic agents may be combined with a surfactant. Some surfactants, such as CHAPS and CHAPSO are zwitterionic but are not counted among the species producing the disclosed effect because the charges are situated close to one another, not at opposite ends of the molecule, and thereby do not create a strong dipole moment and thus lack the ability to elevate the dielectric constant of the medium.

In some embodiments, glycine or other zwitterionic agents may be combined with conventional inorganic buffers and salts. In some such embodiments, the buffers may include commonly used agents such as sodium and/or potassium phosphate, sodium and/or potassium chloride, and other inorganic buffers and salts.

In some embodiments, glycine or other zwitterionic agents may be combined with sugars, including monosaccharides and polysaccharides. In some such embodiments, these may include sugars such as mannitol, sorbitol, sucrose, trehalose, or other sugars.

In some embodiments, glycine or other zwitterionic agents combined with buffers such as Hepes or IVIES. Although these are marketed as zwitterionic buffers, they are not properly zwitterionic at the pH values where they are employed, because at least one of the charged residues is partly titrated. Accordingly, they do not contribute to the beneficial effect of the disclosed process.

In some embodiments, glycine or other zwitterionic agents may be combined with organic solvents or polymers, including glycerol, ethylene glycol, propylene glycol, dimethyl sulfoxide, polyethylene glycol, polypropylene glycol, or polyvinylpyrrolidone, or others.

In some embodiments, glycine or other zwitterionic agents may be combined with specific species of metal ions. In some such embodiments the metal species may one or more selected from the group consisting of calcium, magnesium, iron, other species of metal ions, or combinations of more than one species of metal ions.

In some embodiments, glycine or other zwitterionic agents may be combined with specific species of chelating agents. In some such embodiments the chelating species may one or more from the group including EDTA (ethylenediaminetetraacetic acid), EGTA (ethyleneglycoltetraacetic acid), TREN, (Tris(2-aminoethyl)amine), other chelating agent, or combinations of chelating agents.

In some embodiments, glycine or other zwitterionic agents when used in conjunction with other substances may employ a concentration of such other substances that is reduced to permit a sufficiently high concentration of glycine without exceeding the limits of physiological osmolarity. In one such embodiment, the concentration of salts, for example, may be reduced so that the conductivity of the composition is below the normal physiological value of about 15 mS/cm. In one such embodiment, a concentration of sodium chloride, in particular, may be reduced to about 25 mM, and the concentration of phosphate buffer may be limited to about 20 mM, so that the concentration of glycine can be about 75 mM without grossly exceeding an osmolarity target of about 250 to about 300 mOsm/kg. In another such embodiment, the concentration of sodium chloride may be reduced to about 50 mM, in combination with about 20 mM phosphate, so that the concentration of glycine can be about 50 mM. In some embodiments, the concentration of sugars or other osmotic agents may be similarly managed.

In some embodiments, glycine or other zwitterionic agents when combined with exosomes may be processed under conditions where glycine may be supplied continuously so that exosomes are always in the presence of glycine. In other embodiments, glycine may be present with exosomes during at least one stage of purification, but need not be present continuously.

In some embodiments, glycine or other zwitterionic agents used in conjunction with exosomes may include use in preparations that contain unpurified, partially purified, or highly purified exosomes.

DEFINITIONS

The terms below are defined so that the invention may be understood more readily. Additional definitions are set forth throughout the detailed description.

"Zwitterion" refers to a molecule having separate and distinct positively and negatively charged moieties resident on the same molecule. Zwitterions include a wide range of amino acids and amino acid polymers containing two or more amino acid subunits, where the respective subunits in a particular polymer may be identical or distinct from one another.

"Exosome" refers to a cell-derived vesicle with a diameter of 30 to 100 nm such as are present in many biological fluids, including cell cultures.

"Osmolarity" refers to the osmotic concentration of one or more osmotically active substances in solution, expressed as osmoles of solute particles per liter of solution. Osmolarity of a solution is often a critical parameter for the functionality and/or stability of a biomolecule or biomolecular assemblage.

"Osmole" refers to a unit of osmotic pressure equivalent to the amount of solute that dissociates in solution to form one mole (Avogadro's number) of particles (molecules and ions).

In some embodiments, a method of isolating exosomes comprises conducting at least one purification step in the presence of an organic zwitterion having a molecular weight of less than about 350 Daltons, wherein a buffering pK of a negatively charged portion of the organic zwitterion is at least one full pH unit below an operating pH at which the at least one purification step is conducted, and a buffering pK of the positively charged portion of the organic zwitterion is at least one full pH unit above the operating pH.

In some embodiments, the organic zwitterion comprises a positively charged nitrogen group and a negatively charged group distal to the positively charge nitrogen group on the organic zwitterion such that there is a separation by at least one carbon atom.

In some embodiments, the at least one carbon atom comprises an uncharged side chain.

In some embodiments, the molar dielectric increment of the organic zwitterion under operating conditions of the at least one purification step is greater than 20. In some embodiments the molar dielectric increment of the organic zwitterion under operating conditions of the at least one purification step is greater than about 17. In some embodiments, the molar dielectric increment is that of glycine, which has been indicated to be in a range from about 18 (older measurements) to about 22.6. See, for example, on the world-wide web at bio.groups.et.byu.net/Dielectric_Increments.phtml.

In some embodiments, wherein the organic zwitterion is an amino acid or peptide comprising from 2 to 5 amino acids, the amino acid or peptide amino acids being selected from the group consisting of glycine, alanine, N,N,N-trimethylglycine, i.e., betaine, and taurine.

In some embodiments, the at least one organic zwitterionic agent is glycine or alanine.

In some embodiments, a concentration of the organic zwitterion is selected from the group consisting of (a) from about 20 mM to about 50 mM, (b) from about 50 mM to about 100 mM, (c) from about 100 mM to about 300 mM, (d) from about 300 mM to about 3 M, and (e) saturated. In some embodiments, the concentration can be any intermediate values or ranges in between.

In some embodiments, a concentration of the organic zwitterion is selected from the group consisting of (a) from about 5 mM to about 20 mM, (b) from about 20 mM to about 50 mM, (c) from about 50 mM to about 100 mM, (d) from about 100 mM to about 300 mM, (e) from about 300 mM to about 3 M, and (f) saturated. In some embodiments, the concentration can be any intermediate values or ranges in between.

In some embodiments, before conducting the at least one purification step, the exosomes are unpurified, partially purified, or highly purified. In some such embodiments, the level of purification is about 5%, 10%, 20%, 40%, 80%, 90%, 95%, 99%, or about 99.9% purified. That is, any level of purification can be obtained prior to the at least one purification step. In some embodiments, the levels of purity of the exosomes represent less than 1% of the contaminant mass, more than 1% of the contaminant mass, more than 10% of the contaminant mass, more than 50% of the contaminant mass, more than 90% of the contaminant mass, more than 95% of the contaminant mass, or more than 99% of the contaminant mass, or intermediate values within those ranges.

In some embodiments, the osmolarity during the at least one purification step is in a range from about 250 milliOsmoles/kg to about 300 milliOsmoles/kg.

In some embodiments, the osmolarity during the at least one purification step is less than about 250 milliOsmoles/kg.

In some embodiments, the osmolarity during the at least one purification step is greater than about 300 milliOsmoles/kg. In some embodiments, the osmolarity is in a range from about 250 to about 300, although zwitterions may have a beneficial effect also at higher and lower concentrations.

In some embodiments, the at least one purification step comprises a filtering step.

In some embodiments, the at least one purification step comprises a chromatography step.

In some embodiments, the at least one purification step comprises a field flow fractionation step.

In some embodiments, the at least one purification step comprises a centrifugation step.

A useful starting point in development of specific compositions for use in the methods disclosed herein is to equilibrate an aqueous preparation of exosomes with a buffer containing 100 mM glycine. The buffer may embody a so-called physiological osmolarity of about 280 to about 310 milliOsmoles per liter. Lacking an osmometer, one example of an appropriate starting point might be 20 mM Hepes, 25 mM NaCl, 100 mM glycine, pH 7.0. Another example might be 50 mM Hepes, 50 mM NaCl, 50 mM glycine, pH 7.0. Hepes might be substituted by another zwitterionic buffer such as histidine, or a mixture of zwitterionic buffers. NaCl may be substituted by an alternative salt, or a mixture of alternative salts. Glycine might be substituted by another zwitterionic species, or combination of zwitterionic species.

In some embodiments, the amount of a given zwitterionic species or mix of zwitterionic species used to produce a beneficial effect may be determined by running a process, such as size exclusion chromatography, followed by an analytical method that allows accurate quantitation of exosomes. In methods disclosed herein, experiments can be run in iterations where each experiment employs an individual species of zwitterionic species at a fixed concentration such as about 10, about 20, about 40, about 80, or about 160 mM, or other concentrations. In some embodiments, methods may be run using a combination of zwitterionic species where the combined zwitterionic species concentration is about 10, about 20, about 40, about 80, or about 160 mM. Subsequent processing steps can be run to identify the minimum effective concentration within whatever tolerances are desired. In some embodiments, a concentration of sodium chloride or other salts may also be varied. In some embodiments, the concentration of the buffering ion may also be varied. In some embodiments, pH may be varied, generally within a range from 6.5 to 7.5. It will be recognized that statistical techniques such as Design of Experiments (DoE) may be employed to dramatically reduce the number of processing variables to obtain valid results where multiple variables are being evaluated.

In some embodiments, an unpurified preparation may be equilibrated to a zwitterion-containing solution by diafiltration, where the process of diafiltration also has the effect of removing some contaminants by their passage through pores in the membrane.

In some embodiments, exosomes may be sedimented by centrifugation and may be equilibrated to a zwitterion-containing environment by re-suspending them in a zwitterion-containing buffer.

In some embodiments, zwitterions may be added to an exosome-containing preparation by direct addition of dry zwitterions, or addition of a concentrated solution containing at least zwitterionic species.

In some embodiments, an exosome preparation may be equilibrated to a zwitterion-containing solution prior to its preservation by a method that effectively removes the water from the preparation, such as simple drying, lyophilization, vitrification, or other method.

EXAMPLES

Example 1

Processing a combination of exosomes and glycine by size exclusion chromatography (SEC). A 30 mL column of Sephacryl S-400 HR, 1.6 cm wide by 15 cm high was equilibrated with a buffer containing 25 mM Hepes, 100 mM glycine, 150 mM NaCl, pH 7.0. A sample consisting of 7 mL of an aqueous preparation of exosomes concentrated by tangential flow microfiltration and containing contaminants with a combined UV absorbance roughly equivalent to the exosomes was applied to the column, and fractionation was conducted in that buffer supplied to the column at a linear flow rate of 60 cm/hr. The run was repeated substituting 1 M glycine for 100 mM glycine. A control was performed, absent glycine, using a buffer of 25 mM Hepes, 150 mM NaCl, pH 7.0. Analysis by NanoSight showed that the processes run with 100 mM glycine gave an exosome recovery of about 99%. The 1 M glycine experiment gave a recovery of about 95%, and the control lacking glycine gave a recovery of about 90%. Exosome quantitation by UV absorbance at the peak summit, showed relative recoveries of about 100%, about 92%, and about 67%, respectively. About 95% of all protein contaminants were eliminated in all experiments. This example indicates two means by which exosome recovery may be estimated. It will be apparent to the person of skill in the art that similar methods could be used to measure exosome recovery after compositions of matter containing exosomes and zwitterions are contacted with other surfaces, and/or under other conditions.

Example 2

Processing of exosomes by size exclusion chromatography in 100 mM glycine. Exosomes concentrated by ultrafiltration were applied to an SEC column identical to the column described in Example 1, but the exosomes were equilibrated to 25 mM Hepes, 25 mM NaCl, 100 mM glycine, at pH 7.0. Exosome recovery, as measured by Nanosight, was about 99%. Non-exosome protein content was reduced by about 95%.

It will be apparent to the person of skill in the art that similar effects will be achieved for all purification methods where fractionation is based on size, and equally for all purification methods where fractionation is based on charge, such as ion exchange chromatography, since the effects of zwitterions-mediated elevation of dielectric constant should be transparent with respect to purification method.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of isolating exosomes comprising: conducting at least one purification step in the presence of an organic zwitterion having a molecular weight of less than about 350 Daltons, wherein a buffering pK of a negatively charged portion of the organic zwitterion is at least one full pH unit below an operating pH at which the at least one purification step is conducted, and a buffering pK of a positively charged portion of the organic zwitterion is at least one full pH unit above the operating pH, wherein the organic zwitterion is an amino acid or a peptide comprising from 2 to 5 amino acids, the amino acid or peptide amino acids being selected from the group consisting of glycine, alanine, N,N,N-trimethylglycine (betaine), and taurine.

2. The method of claim 1, wherein a molar dielectric increment of the organic zwitterion under the operating conditions of the at least one purification step is greater than about 17.

3. The method of claim 1, wherein the at least one organic zwitterion is glycine or alanine.

4. The method of claim 1, wherein a concentration of the organic zwitterion is from about 20 mM to about 3 M, or saturated.

5. The method of claim 4, wherein the concentration of the organic zwitterion is selected from the group consisting of (a) from about 5 mM to about 20 mM, (b) from about 20 mM to about 50 mM, (c) from about 50 mM to about 100 mM, (d) from about 100 mM to about 300 mM, (e) from about 300 mM to about 3 M, and (f) saturated.

6. The method of claim 1, wherein before conducting the at least one purification step, the exosomes are unpurified, partially purified, or purified.

7. The method of claim 1, wherein an osmolarity during the at least one purification step is in a range from about 250 milliOsmoles/kg to about 300 milliOsmoles/kg.

8. The method of claim 1, wherein an osmolarity during the at least one purification step is less than 250 milliOsmoles/kg.

9. The method of claim 1, wherein an osmolarity during the at least one purification step is greater than 300 milliOsmoles/kg.

10. The method of claim 1, wherein the at least one purification step comprises a filtering step.

11. The method of claim 1, wherein the at least one purification step comprises a chromatography step.

12. The method of claim 1, wherein the at least one purification step comprises a field flow fractionation step.

13. The method of claim 1, wherein the at least one purification step comprises a centrifugation step.

14. The method of claim 11, wherein the chromatography step comprises a size exclusion chromatography step.

15. The method of claim 14, wherein the organic zwitterion is glycine or alanine at a concentration of 20 mM to 300 mM.

16. The method of claim 14, wherein the at least one purification step comprises contacting a sample comprising exosomes with a size exclusion chromatography media in the presence of the organic zwitterion, wherein the organic zwitterion is in a soluble form.

17. The method of claim 16, wherein the sample, prior to conducting of the at least one purification step, comprises non-exosome proteins, and the method further comprises, after the conducting of the at least one purification step, providing isolated exosomes, wherein the isolated exosomes comprise at least 95% of the exosomes in the sample and less than 5% of the of the non-exosome proteins in the sample.

18. A method of isolating exosomes comprising: conducting at least one purification step in the presence of an organic zwitterion having a molecular weight of less than about 350 Daltons, wherein a buffering pK of a negatively charged portion of the organic zwitterion is at least one full pH unit below an operating pH at which the at least one purification step is conducted, and a buffering pK of a positively charged portion of the organic zwitterion is at least one full pH unit above the operating pH, wherein the at least one purification step comprises a filtering step, a field flow fractionation step, a centrifugation step, or a size exclusion chromatography step.

19. The method of claim 18, wherein the at least one purification step comprises contacting a sample comprising exosomes with a size exclusion chromatography media in the presence of the organic zwitterion, wherein the organic zwitterion is in a soluble form.

20. The method of claim 18, wherein the organic zwitterion comprises a positively charged nitrogen group and a negatively charged group distal to the positively charged nitrogen group on the organic zwitterion such that there is a separation by at least one carbon atom.

21. The method of claim 20, wherein the at least one carbon atom comprises an uncharged side chain.

* * * * *